US012313593B2

(12) United States Patent
Reider et al.

(10) Patent No.: US 12,313,593 B2
(45) Date of Patent: May 27, 2025

(54) METHOD AND DEVICE FOR DETERMINING ANTIFREEZE CONTENT IN A FLUID OF AN HVAC SYSTEM

(71) Applicant: BELIMO HOLDING AG, Hinwil (CH)

(72) Inventors: Forest Reider, Hinwil (CH); Stefan Mischler, Wald (CH); Volkher Scholz, Zürich (CH); Philip Holoch, Neschwil (CH)

(73) Assignee: BELIMO HOLDING AG, Hinwil (CH)

( * ) Notice: Subject to any disclaimer, the term of this patent is extended or adjusted under 35 U.S.C. 154(b) by 196 days.

(21) Appl. No.: 17/802,284

(22) PCT Filed: Apr. 27, 2021

(86) PCT No.: PCT/EP2021/060967
§ 371 (c)(1),
(2) Date: Aug. 25, 2022

(87) PCT Pub. No.: WO2021/219627
PCT Pub. Date: Nov. 4, 2021

(65) Prior Publication Data
US 2023/0146901 A1 May 11, 2023

(30) Foreign Application Priority Data
Apr. 28, 2020 (CH) .......................... 497/20

(51) Int. Cl.
*G01N 29/024* (2006.01)
*G01N 29/44* (2006.01)

(52) U.S. Cl.
CPC ....... *G01N 29/024* (2013.01); *G01N 29/4418* (2013.01); *G01N 2291/0222* (2013.01); *G01N 2291/02809* (2013.01)

(58) Field of Classification Search
CPC ............ G01N 29/024; G01N 29/4418; G01N 33/1826; G01N 2291/0222; G01N 2291/02809
(Continued)

(56) References Cited

U.S. PATENT DOCUMENTS

| 5,473,934 A | 12/1995 | Cobb | |
| 2013/0259083 A1* | 10/2013 | Lindgren | G01K 17/08 374/29 |

FOREIGN PATENT DOCUMENTS

| EP | 2 369 305 A1 | 9/2011 |
| EP | 3 301 440 A1 | 4/2018 |

OTHER PUBLICATIONS

Thannhaeuser et al., EP 3301440 A1, "Liquid Retention System With an Ultrasound Sensor", Date published: Apr. 4, 2018 (Year: 2018).*

(Continued)

*Primary Examiner* — John H Le
(74) *Attorney, Agent, or Firm* — Sughrue Mion, PLLC

(57) ABSTRACT

A method for determining antifreeze content in a fluid of a heating, ventilation, and air conditioning (HVAC) system includes receiving, in a processor, measurement data of the fluid, the measurement data comprising a measured temperature of the fluid and a measured speed of sound in the fluid, calculating, in the processor, for each of a plurality of antifreeze concentration values a fitting parameter, using the measurement data and one or more of previous measurement data or previous antifreeze concentration data, and determining, in the processor, an antifreeze concentration in the fluid by selecting the antifreeze concentration value with an optimal fitting parameter.

15 Claims, 7 Drawing Sheets

(58) Field of Classification Search
USPC .......................................................... 702/54
See application file for complete search history.

(56) References Cited

OTHER PUBLICATIONS

International Search Report for PCT/EP2021/060967 dated Jul. 1, 2021.
Written Opinion for PCT/EP2021/060967 dated Jul. 1, 2021.
Swiss Search Report of CH 4972020 dated Jul. 28, 2020.

* cited by examiner

METHOD AND DEVICE FOR DETERMINING ANTIFREEZE CONTENT IN A FLUID OF AN HVAC SYSTEM

CROSS REFERENCE TO RELATED APPLICATIONS

This application is a National Stage of International Application No. PCT/EP2021/060967 filed Apr. 27, 2021, claiming priority based on Swiss Patent Application No. 00497/20 filed Apr. 28, 2020, the contents of each of which being herein incorporated by reference in their entireties.

FIELD OF THE INVENTION

The present invention relates to a method and device for determining antifreeze content in a fluid of an HVAC system. In particular, the present invention relates to a method, a device comprising a processor, and a computer program product for determining antifreeze content in a fluid of an HVAC system.

BACKGROUND OF THE INVENTION

Systems for heating, ventilation, and air conditioning (HVAC) often use a fluid to transport heat to and/or from a heat exchanger. Although pure water could be considered an excellent candidate as a fluid for an HVAC system because of its large heat capacity and non-toxicity, it is often mixed in a binary mixture with an additional fluid, such as an antifreeze, to increase the range of operating temperatures of the fluid, as the operating temperatures are limited by the boiling temperature of the fluid and the freezing temperature of the fluid. A well-known antifreeze is glycol, which comes in varieties such as propylene glycol and ethylene glycol. Others include brine (water/salt mixture). By using a water/glycol mixture the freezing temperature of the fluid is reduced and the boiling temperature of the fluid is increased. In addition to the water/glycol components, small amounts of additives may also be added to the fluid, such as stabilizers, corrosion inhibitors, reducing agents (oxygen traps), and anti-fouling agents.

It is important to know the mixing ratio of water and antifreeze, as well as the type of antifreeze used, to be able to accurately determine how much heat is being transported by the fluid and also to determine the range of operating temperatures of the HVAC system. If too much glycol is present, for example, then the efficiency of the HVAC system is reduced. This is because glycol has a higher viscosity than water, and therefore more pumping energy is required at higher glycol proportions. Further, glycol has worse heat transfer than water and is also more expensive. For these reasons it is important to know the mixing ratio of water/glycol. Typically, HVAC systems can have mixing ratios of up to 60%. The mixing ratio in the HVAC system can slowly change over time. The mixing ratio can also change quickly when water and/or antifreeze is refilled in the HVAC system. To ensure reliable and predictable operation of the HVAC system, it is therefore important to periodically determine the antifreeze content in the fluid.

SUMMARY OF THE INVENTION

It is an object of this invention to provide a method and device for determining antifreeze content in a fluid of an HVAC system. In particular, is an object of this invention to provide a method, a device comprising a processor, and a computer program product for determining antifreeze content in a fluid of an HVAC system.

According to the present invention, these objects are achieved through the features of the independent claims. In addition, further advantageous embodiments follow from the dependent claims and the description.

According to the present invention, the above-mentioned objects are particularly achieved by a method for determining antifreeze content in a fluid of an HVAC system, the method comprising receiving, in a processor, measurement data of the fluid, the measurement data comprising a measured temperature of the fluid and a measured speed of sound in the fluid. The method comprises calculating, in the processor, for each of a plurality of antifreeze concentration values a fitting parameter, using the measurement data and at least one of: previous measurement data or previous antifreeze concentration data. The method comprises determining, in the processor, an antifreeze concentration in the fluid by selecting the antifreeze concentration value with an optimal fitting parameter.

In an embodiment, calculating the fitting parameter for each of the plurality of antifreeze concentration values proceeds iteratively comprising calculating, in the processor, for an initial set of antifreeze concentration values an initial set of fitting parameters and generating, in the processor, using the antifreeze concentration value of the initial set of antifreeze concentration values with an optimal fitting parameter, a subsequent set of antifreeze concentration values. Calculating the fitting parameter comprises calculating, in the processor, using the subsequent set of antifreeze concentration values a subsequent set of fitting parameters; and determining, in the processor, the antifreeze concentration in the fluid by selecting the antifreeze concentration value of the subsequent set of antifreeze concentration values with a subsequent optimal fitting parameter.

In an embodiment, calculating, in the processor, the fitting parameter for each of the plurality of antifreeze concentration values comprises using a defined relation between antifreeze concentration, temperature, and speed of sound.

In an embodiment, the method further comprises determining, in the processor, using the measurement data, the plurality of antifreeze concentration values such that each of the plurality of antifreeze concentration values satisfies a defined relation between antifreeze concentration, temperature, and speed of sound.

In an embodiment, the method further comprises determining, in the processor, if only one antifreeze concentration value is determined, the antifreeze concentration in the fluid to have that antifreeze concentration value and, if more than one antifreeze concentration value is determined, then in the processor, calculating the fitting parameter.

In an embodiment, each antifreeze concentration value is associated with an antifreeze type and the method further comprises identifying the antifreeze type in the fluid by determining, in the processor, the antifreeze type associated with the determined antifreeze concentration.

In an embodiment, the antifreeze type is determined further using previous antifreeze type data, the previous antifreeze data being retrieved by the processor 21 from the memory 22. The previous antifreeze type data relates to previously determined antifreeze types in the fluid. Additionally, data entries relating to specified antifreeze types are also contained in the previous antifreeze type data. When determining the antifreeze type in the fluid currently, the previous antifreeze type data is weighted heavily. This is because the antifreeze type cannot change spontaneously from one day to the next, it normally requires manual intervention in the HVAC system.

In an embodiment, calculating the fitting parameter for each antifreeze concentration value comprises calculating, in the processor, a predictor using the previous measurement data and/or previous antifreeze concentration data, and comparing, in the processor, the predictor with the measurement data and/or the antifreeze concentration values.

In an embodiment, calculating the fitting parameter for each antifreeze concentration value comprises calculating, in the processor, one or more sums of differences by comparing one or more of the following: the measured temperature with the previous temperature data, the measured speed of sound with the previous speed of sound data, and the antifreeze concentration value with the previous antifreeze concentration data.

In an embodiment, calculating the fitting parameter for each antifreeze concentration value comprises the processor calculating one or more partial derivatives. For example, partial derivatives of the speed of sound with respect to the temperature are calculated by the processor.

In an embodiment, the partial derivative of the speed of sound with respect to the temperature at a particular antifreeze concentration is calculated, in the processor, by computing a difference between successive speeds of sound and dividing this difference by a difference between successive temperatures In an embodiment, a measured partial derivative and a predicted partial derivative are computed, the measured partial derivative computed by the processor using the measured speed of sound, previously measured speeds of sound, the measured temperature, and previously measured temperatures. The predicted partial derivative is computed, in the processor, by computing a predicted speed of sound using the measured temperature and the defined relation, and dividing the difference between two successive predicted speeds of sound with a difference between two successive temperature measurements.

In an embodiment, the relation further includes a differentiated relation between the temperature, the concentration and the partial derivative. This is then used to determine the predicted partial derivative.

In an embodiment, the measured partial derivative and the predicted partial derivative are computed for each of the antifreeze concentration values, and the processor calculates the fitting parameter for each antifreeze concentration using a difference between the measured partial derivative and the predicted partial derivative.

In an embodiment, the sums of differences are weighted, for example using an exponential weighting such that more recent previous measurement data is weighted greater than less recent measurement data and more recent previous antifreeze concentration data is weighted greater than less recent previous antifreeze concentration data.

In an embodiment, the weighted sum of differences uses differences between successive measurements of the previous measurement data and/or between successive antifreeze concentrations of the previous antifreeze concentration data.

In an embodiment, calculating the fitting parameter for each antifreeze concentration value comprises determining, in the processor, using previous measurement data and previous antifreeze concentration data, moving average values comprising one or more of the following: a moving temperature average, a moving speed of sound average, and a moving antifreeze concentration average. The method comprises comparing, in the processor, one or more of the following: the measured temperature with the moving temperature average, the measured speed of sound with the moving speed of sound average, and the antifreeze concentration value with the moving antifreeze concentration average.

In an embodiment, calculating the fitting parameter for each antifreeze concentration value comprises estimating, in the processor, a predicted speed of sound and/or a predicted change in the speed of sound, respectively the partial derivative of the speed of sound, using the measured temperature and the defined relation, and comparing, in the processor, the predicted speed of sound with the measured speed of sound. In an embodiment, the method further comprises detecting, in the processor, a change in the measurement data, and determining the antifreeze content in the fluid, including the antifreeze concentration and/or the antifreeze type, upon detection of a change in the measurement data.

In an embodiment, the method further comprises receiving, in the processor, a refill indicator, the refill indicator indicating a point in time that the fluid in the HVAC system has been refilled. The method comprises calculating the fitting parameter using the refill indicator.

In an embodiment, the method further comprises determining a change of antifreeze concentration in the fluid by comparing, in the processor, the determined antifreeze concentration in the fluid with previous antifreeze concentration data and generating, in the processor, a message indicating the change of antifreeze concentration in the fluid.

In addition to the method for determining antifreeze content in a fluid of an HVAC system, the present invention also relates to a device for determining antifreeze content in a fluid of an HVAC system, the device comprising a processor configured to receive measurement data of the fluid, the measurement data comprising a measured temperature of the fluid and a measured speed of sound in the fluid. The processor is configured to calculate, for each of a plurality of antifreeze concentration values a fitting parameter, using the measurement data and at least one of: previous measurement data or previous antifreeze concentration data; and determine the antifreeze concentration in the fluid by selecting the antifreeze concentration value with an optimal fitting parameter.

In an embodiment, the processor is configured to calculate the fitting parameter for each of the plurality of antifreeze concentration values iteratively. The processor is configured to calculate, for an initial set of antifreeze concentration values an initial set of fitting parameters; generate, using the antifreeze concentration value of the initial set of antifreeze concentration values with an optimal fitting parameter, a subsequent set of antifreeze concentration values; calculate, using the subsequent set of antifreeze concentration values a subsequent set of fitting parameters; and determine the antifreeze concentration in the fluid by selecting the antifreeze concentration value of the subsequent set of antifreeze concentration values with a subsequent optimal fitting parameter.

In an embodiment, the processor is configured to calculate the fitting parameter for each of the plurality of antifreeze concentration values using a defined relation between antifreeze concentration, temperature, and speed of sound.

In an embodiment, the processor is further configured to determine, using the measurement data, the plurality of antifreeze concentration values such that each of the plurality of antifreeze concentration values satisfies a defined relation between antifreeze concentration, temperature, and speed of sound.

In an embodiment, if only one antifreeze concentration value is determined, the processor is configured to determine the antifreeze concentration in the fluid to have that antifreeze concentration value, and if more than one antifreeze concentration value is determined, then to calculate the fitting parameter for each antifreeze concentration.

In an embodiment, each antifreeze concentration value is associated with an antifreeze type, and the processor is further configured to identify the antifreeze type in the fluid by determining the antifreeze type associated with the determined antifreeze concentration.

In an embodiment, to calculate the fitting parameter for each antifreeze concentration value, the processor is configured to calculate a predictor using the previous measurement data and/or previous antifreeze concentration data, and compare the predictor with the measurement data and/or the antifreeze concentration values.

In an embodiment, to calculate the fitting parameter for each antifreeze concentration value the processor is configured to calculate one or more weighted sums of differences by comparing one or more of the following: the measured temperature with the previous temperature data, the measured speed of sound with the previous speed of sound data, and the antifreeze concentration value with the previous antifreeze concentration data.

In an embodiment, the processor is configured to calculate the weighted sum of differences by using differences between successive measurements of the previous measurement data and/or between successive antifreeze concentrations of the previous antifreeze concentration data.

In an embodiment, to calculate the fitting parameter for each antifreeze concentration value the processor is configured to determine, using previous measurement data and previous antifreeze concentration data, moving average values comprising one or more of the following: a moving temperature average, a moving speed of sound average, and a moving antifreeze concentration average. The processor is configured to compare one or more of the following: the measured temperature with the moving temperature average, the measured speed of sound with the moving speed of sound average, and the antifreeze concentration value with the moving antifreeze concentration average.

In an embodiment, to calculate the fitting parameter for each antifreeze concentration value the processor is configured to estimate a predicted speed of sound using the measured temperature and the defined relation, and to compare the predicted speed of sound with the measured speed of sound.

In an embodiment, the processor is further configured to detect a change in the measurement data, and to determine the antifreeze content in the fluid, including the antifreeze concentration and/or antifreeze type, upon detection of a change in the measurement data.

In an embodiment, the processor is further configured to receive a refill indicator, indicating a point in time that fluid in the HVAC system has been refilled, and the processor is configured to calculate the fitting parameter using the refill indicator.

In an embodiment, the processor is further configured to determine a change of antifreeze concentration in the fluid by comparing the determined antifreeze concentration in the fluid with previous antifreeze concentration data and, if a change is determined, generate a message indicating the change of antifreeze concentration in the fluid.

In addition to the method and device for determining antifreeze content in a fluid of an HVAC system, the present invention also relates to a computer program product comprising computer program code configured to control a processor of a device such that the device performs the steps of the method as described above. In particular, the method comprising receiving, in a processor, measurement data of the fluid, the measurement data comprising a measured temperature of the fluid and a measured speed of sound in the fluid. The method comprises calculating, in the processor, for each of a plurality of antifreeze concentration values a fitting parameter, using the measurement data and at least one of: previous measurement data or previous antifreeze concentration data. The method comprises determining, in the processor, an antifreeze concentration in the fluid by selecting the antifreeze concentration value with an optimal fitting parameter.

The present invention also relates to a device of an HVAC system configured to receive a relation of a fluid of an HVAC system, a method for receiving in a device of an HVAC system 1 relation of a fluid of an HVAC system, and a computer program product comprising computer program code configured to control a processor of a device of an HVAC system such that the device receives a relation of a fluid of an HVAC system, in particular a relation of a fluid which is a binary mixture, such as a fluid comprising antifreeze. It is commonly known in the field of HVAC systems that many types of antifreeze also have an anti-boil effect, and that therefore the fluid comprising antifreeze also has, depending on the embodiment, a raised boiling point. For example, a water/glycol mixture not only has a lower freezing point than pure water, but also a higher boiling point than pure water. The device comprises a processor and a memory and is embodied, for example, a control device or a sensor unit such as a heat meter.

The relation is associated with a fluid containing a particular type of antifreeze. In an embodiment, the relation comprises characteristic values of the fluid related to one or more of the following: a fluid density, a heat capacity, a speed of sound, or a viscosity, as a function of a fluid temperature and/or a fluid concentration. The characteristic values are, in an embodiment, a table of the characteristic values. The characteristic values include, in an embodiment, function coefficients used to generate the characteristic values as a function of the fluid temperature and/or the fluid concentration.

The device receives the relation via a wired connection, for example a cable of a building management system, or via a wireless connection, for example NFC. The relation is received from a local gateway, from a data storage system, or from a remote server, in particular a remote cloud-based server.

The device is configured to store the relation in the memory of the device. The device is configured to use the received relation. In particular, the device is configured to use the characteristic values to determine, using a measured speed of sound and a measured fluid temperature, the fluid concentration according to a method described herein.

Receiving and storing the relation of the new fluid does not require any previous measurement data or previous antifreeze concentration data to be stored in the memory of the device.

It should be noted that all aspects of the present invention, in particular the device of an HVAC system and the method steps, relate not only to determining a concentration of antifreeze in a fluid of the HVAC system, but also relate to determining a concentration of all types of fluids of an HVAC system which are binary mixtures, and which may have properties such as being antifreeze, anti-boil, anti-corrosion, and/or anti-scaling.

BRIEF DESCRIPTION OF THE DRAWINGS

The present invention will be explained in more detail, by way of example, with reference to the drawings in which.

DETAILED DESCRIPTION OF THE PREFERRED EMBODIMENTS

Figure 1:
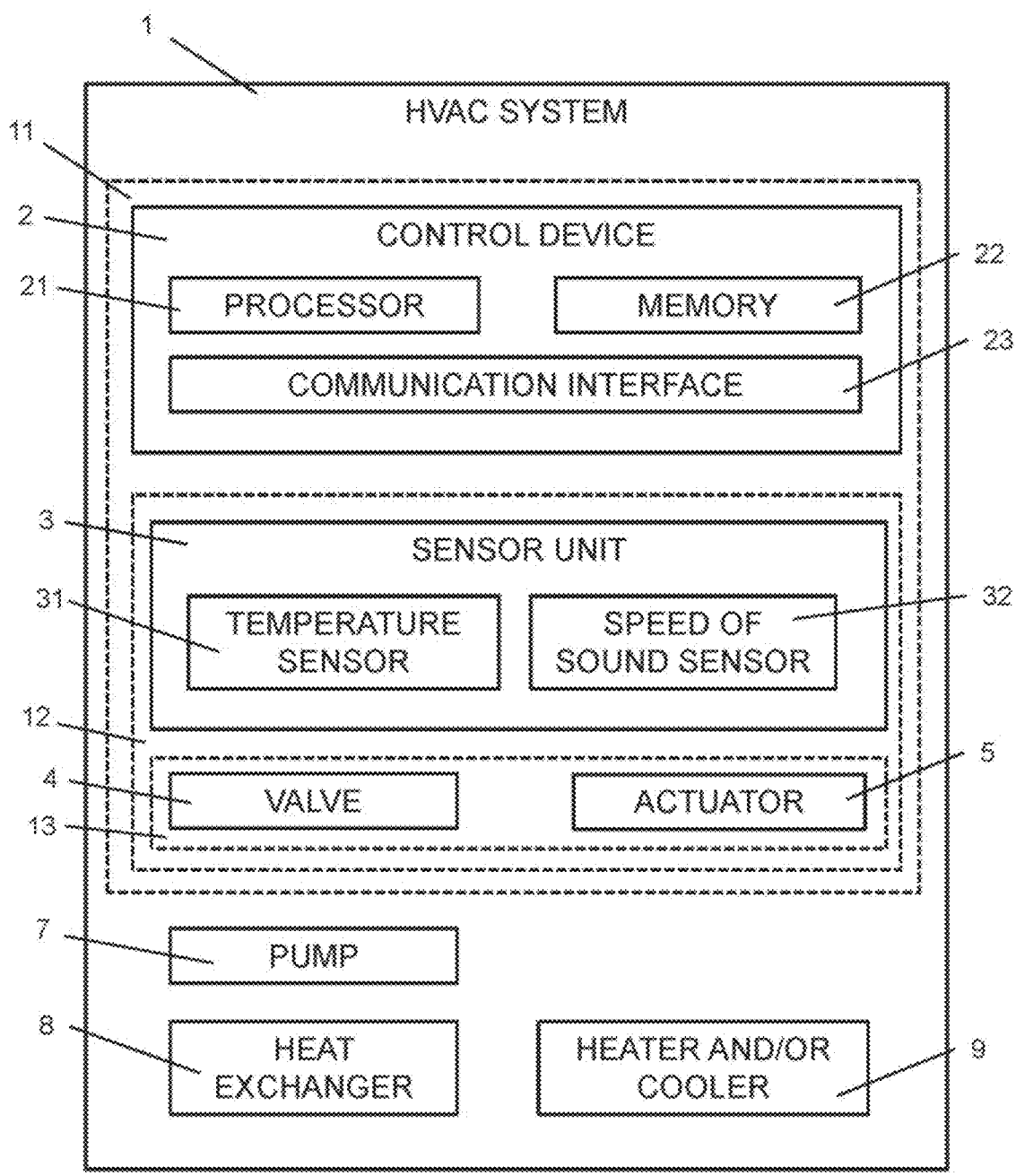
FIG. 1: shows a block diagram illustrating schematically an HVAC system.

In FIG. 1, reference numeral a refers to a heating, ventilation, and air conditioning (HVAC) system. The HVAC system 1 comprises a control device 2 and a sensor unit 3. A valve 4 controls the flow of a binary fluid, more specifically a water/antifreeze mixture, or even more specifically a water/glycol mixture, through the HVAC system 1, in particular through a pipe of the HVAC system 1. The valve 4 is controlled by an actuator 5. The actuator 5 is an electromechanical device comprising an electric motor which, depending on a control signal, alters the opening or closing of the valve 4 to allow more or less, respectively, fluid through the valve 4. The fluid is driven through the HVAC system 1 by a pump 7. The fluid flows through a heater and/or a cooler g, which heats or cools the fluid. The fluid also flows through a heat exchanger 8. The heat exchanger 8 deposits or absorbs heat from the fluid into an environment around the heat exchanger 8.

In an embodiment, the HVAC system 1 comprises more than one pump 7, heater and/or cooler g, or heat exchanger 8.

In some embodiments, one or more components of the HVAC system 1 as described above are integrated together.

In an embodiment, the valve 4 and the actuator 5 are arranged in a single device, as indicated by the dashed box 13.

In an embodiment, the sensor unit 3, the valve 4, and the actuator 5 are arranged in a single device, as indicated by the dashed box 12.

In a preferred embodiment the control device 2 and the sensor unit 3 are part of a single device.

In an embodiment, the control device 2, the sensor unit 3, the valve 4, and the actuator 5 are integrated into a single device, as indicated by the dashed box 11.

In an embodiment, the sensor unit 3 also comprises a controller and a memory, and one or more functions and/or steps as described in the present disclosure are performed in the sensor unit 3 by the controller. Further, certain data as described in the present disclosure are stored in the memory of the sensor unit 3.

The sensor unit 3 comprises one or more sensors configured to measure the fluid, more particularly to measure physical properties of the fluid. The sensor unit comprises one or more of the following sensors: a temperature sensor 31 and a speed of sound sensor 32. The temperature sensor 31 is configured to measure a temperature of the fluid and is, in an example, a thermistor or a resistive temperature detector (RTD). A temperature sensing element of the temperature sensor 31 is either in direct contact or in indirect contact with the fluid. The speed of sound sensor 32 measures a speed of sound in the fluid. In an embodiment, the speed of sound sensor 32 comprises a first and a second ultrasonic transducer, and a transit time of an ultrasonic pulse traveling between the first and the second ultrasonic transducer is used to determine the speed of sound in the fluid.

In an embodiment, the sensor unit 3 is part of a heat meter and comprises an additional temperature sensor, which allows the sensor unit 3 to measure a temperature difference and allow the sensor unit 3 and/or the control device 2 to determine the heat transferred by the heat exchanger 8. The calculation of the heat transfer is performed either by the controller in the sensor unit 3 itself, or in the control unit 2.

The sensor unit 3 is connected to the control device 2. The sensor unit 3 is configured to send measurement data to the control device 2, which the control device 2 receives. The sensor unit 3 is configured to receive measurement commands from the control device 2, upon receipt of which the sensor unit 3 carries out measurements and transmits measurement data to the control device 2.

In an embodiment, the sensor unit 3 continuously carries out measurements at predetermined intervals. When the control device 2 queries the sensor unit 3, the sensor unit 3 transmits measurement data to the control device 2.

Figure 2:
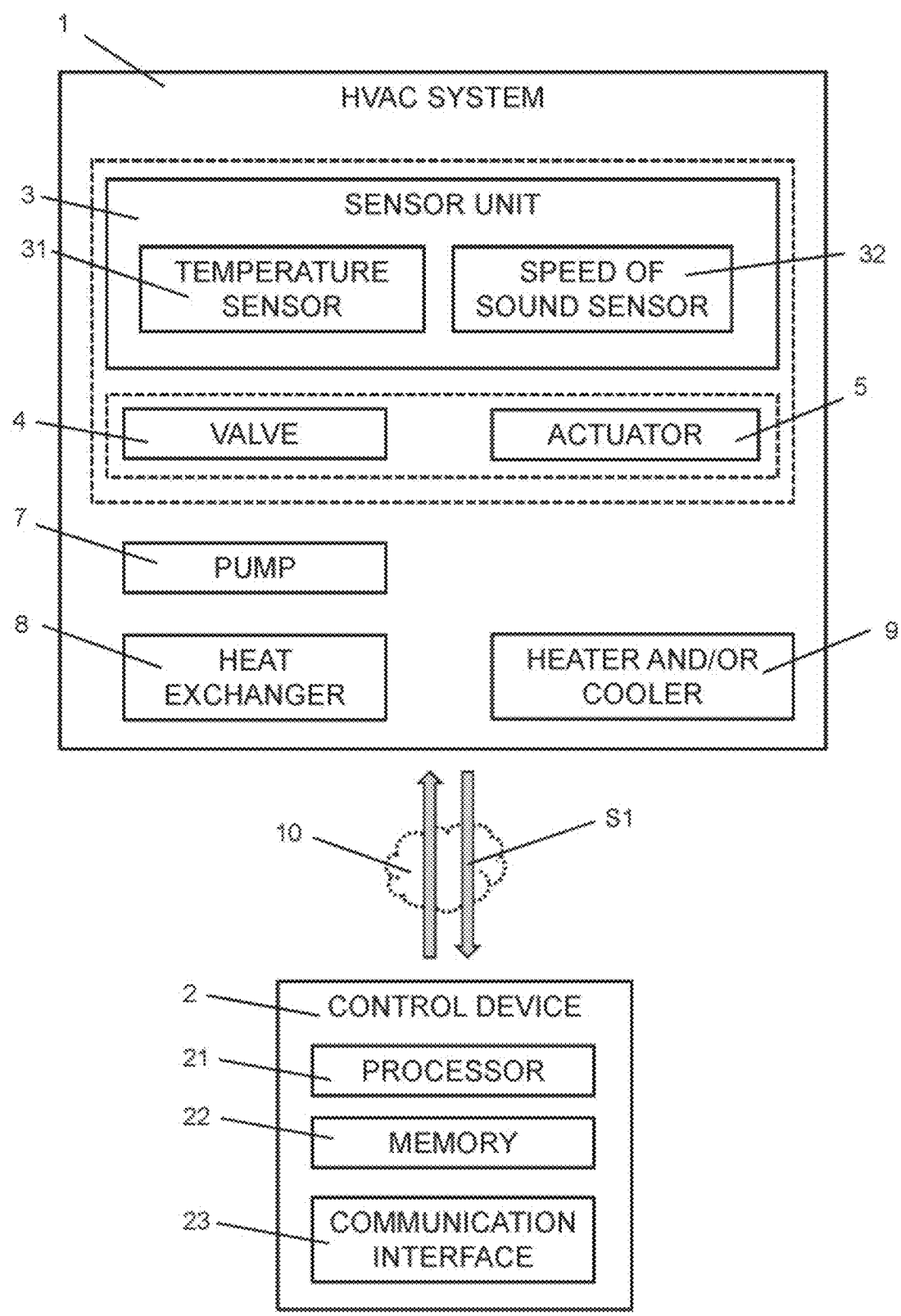
FIG. 2: shows a diagram illustrating schematically an HVAC system with a separate control device.

The control device 2 comprises an electronic circuit including a processor 21 and various modules. The modules include a memory 22 and a communication interface 23, for example a BACnet and/or Modbus interface. Depending on the embodiment, the modules further include a display, a battery, and/or a user interface. The battery can also be part of the sensor unit 3. The user interface can be integrated into the display in the form of a touch-sensitive display. The user interface, in an example, comprises buttons. The modules of the control device 2 are connected to each other via a data connection mechanism, such that they can transmit and/or receive data. The communication interface 23 is configured for wired and/or wireless communication with the sensor unit 3. The control device 2 is also connected to one or more of: the actuator 5, the pump 7, or the heater and/or cooler g and is configured to transmit control signals to these for controlling the operation of the HVAC system 1. Depending on the embodiment, the communication interface 23 is configured to communicate with remote servers via a communication network 10. The communication network 10, as depicted in FIG. 2 below, comprises the Internet as well as other intermediary networks. The wireless communication takes place using a mobile data network, such as GSM, CDMA and LTE networks, and/or a close range wireless communication interface using a Wi-Fi network, Bluetooth, NFC, and/or other wireless network type and standard. In an example, the processor 21 provides an internal webserver which hosts a webpage, the webpage providing the user interface.

In an embodiment, the control device 2 communicates with the remote servers via a local gateway, which local gateway forwards messages from the control device 2 to the remote servers and vice versa (i.e. the local gateway also forwards messages from the remote servers to the control device 2).

The term data connection mechanism relates to a mechanism that facilitates data communication between two modules, devices, systems, or other entities. The data connection mechanism is a wired connection across a cable or system bus, or wireless connection using direct or indirect wireless transmissions.

Depending on the embodiment, the electronic circuit or the processor 21, respectively, comprises a system on a chip (SoC), a central processing unit (CPU), and/or other more specific processing units such as a graphical processing unit (GPU), application specific integrated circuits (ASICs), reprogrammable processing units such as field programmable gate arrays (FPGAs), as well as processing units specifically configured to accelerate certain applications, such as artificial intelligence (AI) accelerators for accelerating neural network and/or machine learning processes.

The memory 22 comprises one or more volatile (transitory) and or non-volatile (non-transitory) storage components. The storage components may be removable and/or non-removable, and can also be integrated, in whole or in part with the control device 2. Examples of storage components include RAM (Random Access Memory), flash memory, hard disks, data memory, and/or other data stores. The memory 22 has stored thereon computer program code configured to control the processor 21 of the control device 2, such that the control device 2 performs one or more steps and/or functions as described herein. Depending on the embodiment, the computer program code is compiled or non-compiled program logic and/or machine code. As such, the control device 2 is configured to perform one or more steps and/or functions. The computer program code defines and/or is part of a discrete software application. One skilled in the art will understand, that the computer program code can also be distributed across a plurality of software applications. The software application is installed in the control device 2. Alternatively, the computer program code can also be retrieved and executed by the control device 2 on demand. In an embodiment, the computer program code further provides interfaces, such as APIs (Application Programming Interfaces), such that functionality and/or data of the control device 2 can be accessed remotely, such as via a client application or via a web browser. In an embodiment, the computer program code is configured such that one or more steps and/or functions are not performed in control device 2 but in a remote server at a different location to the control device 2, e.g. in a cloud-based computer system.

FIG. 2 shows a diagram illustrating schematically an embodiment of the invention in which the control device 2 is separate from the HVAC system 1 and is connected with the HVAC system 1 using the data connection mechanism. In particular, the communication interface 23 of the control device 2 is connected with the sensor unit 3 of the HVAC system 1 using the data connection mechanism. Further, in an embodiment, the sensor device 3 also has a communication interface configured for wired and/or wireless transmission.

In an embodiment, the control device 2 is connected directly to the HVAC system 1 using the data connection mechanism. In this embodiment, the control device 2 is located at or near the location of the HVAC system 1, such as in the same building or on the same premises as the HVAC system 1. In an example, the control device 2 is implemented as a mobile communication device, for example a mobile phone. The mobile phone, for example a smart-phone running the Android operating system or the iOS operating system, is configured to download and install the computer program code from a server, for example from an App store. Further examples of control devices 2 are tablet computers, smartwatches and the like. Another example of the control device 2 implemented as a mobile communication device is a portable computer, for example a laptop.

In an embodiment, in addition to being connected to the HVAC system 1, the control device 2 is also connected to the remote server via the Internet 10, using the communication interface 23. The connection to the remote server enables the control device 2 to exchange data with the remote server at the same time as exchanging data with the HVAC system 1.

In an embodiment, the control device 2 is located remotely from the HVAC system 1 and is connected to the HVAC system 1 via the Internet 10. In particular, the control device 2 is implemented on the remote server and exchanges data with the sensor unit 3 of the HVAC system 1. Optionally, the local gateway acts as an intermediary between the control device 2 and the sensor unit 3.

Figure 3:
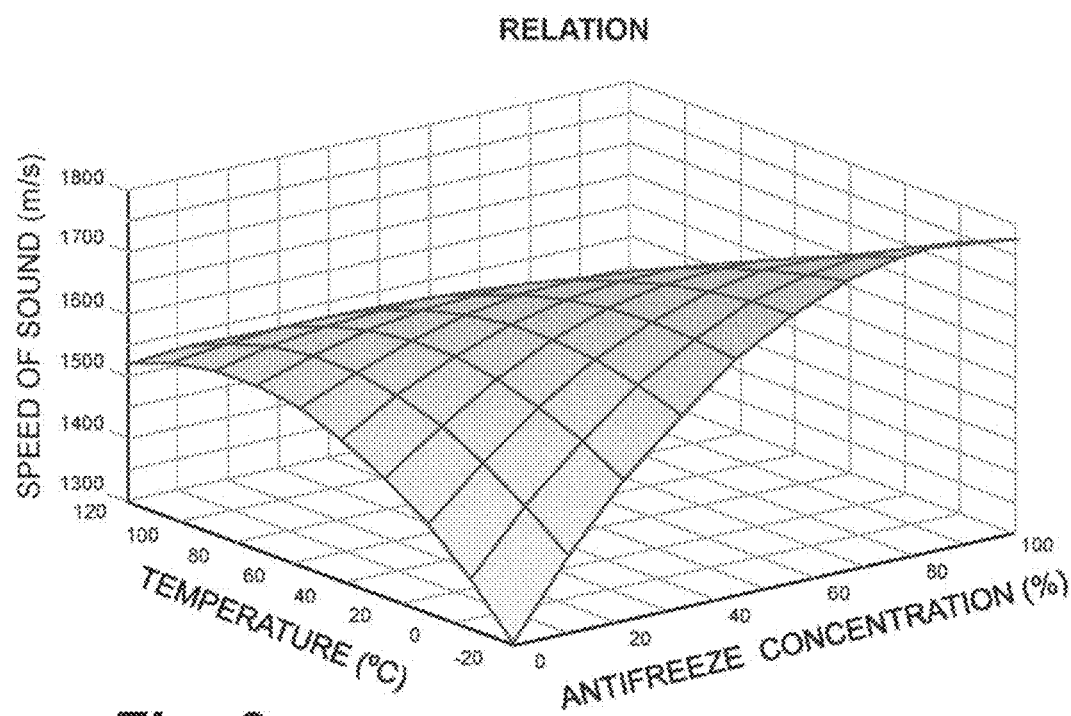
FIG. 3: shows a 3D plot illustrating a relation between temperature, antifreeze concentration, and speed of sound.

FIG. 3 shows a defined relation between temperature in degrees Celsius (° C.), antifreeze concentration in the fluid as a percentage of weight or volume (%), and speed of sound in meters per second (m/s). The relation specifies a set of points in 3D space which correspond to possible physical states of the fluid, wherein the physical states of the fluid are defined by the temperature of the fluid, the antifreeze concentration of the fluid, and the speed of sound in the fluid. Both antifreeze concentration and temperature in the fluid influence the speed of sound in the fluid. Different antifreeze types have different relations between temperature, antifreeze concentration, and speed of sound, and in general, each antifreeze type is associated with a distinct relation. The relation, and therefore the set of points, can be plotted as a geometric shape in the form of a curved two-dimensional surface as illustrated in FIG. 3. FIG. 3 shows a section of such a surface for a particular antifreeze type. As can also be seen by the shading of the surface in FIG. 3, the curvature of the surface is such that, for certain values of temperature, there does not exist an unambiguous mapping between speed of sound and antifreeze concentration. Therefore, a measured temperature of the fluid and a measured speed of sound in the fluid is not necessarily sufficient to unambiguously determine a value of the antifreeze concentration in the fluid.

According to a particular embodiment of the invention, the relation can be stored and/or generated in a variety of ways. The relation can be stored on the control device 2 or retrieved by the control device 2 from the local gateway, from the remote server, or from another data storage system. Each relation is associated with a particular type of antifreeze, such that depending on the embodiment, a plurality of relations are stored for a plurality of antifreeze types.

In an embodiment, the relation is stored as a set of points, in particular as a set of points in a look-up table. In another embodiment, the relation is stored as a function or as set of functions, in particular as one or more polynomial functions. The coefficients of the polynomial functions are stored with the functions or separately from the function.

In an embodiment, further functions, properties and/or quantities are associated with the relation, and these can either be stored or generated as required. These include derivatives of the relation at particular points with respect to particular parameters and/or quantities including maxima, minima, inflection points, etc.

In an embodiment, a new or updated relation is received by the control device 2 from the remote server for a particular antifreeze type and the control device 2 stores the updated relation for the particular antifreeze type.

Figure 4:
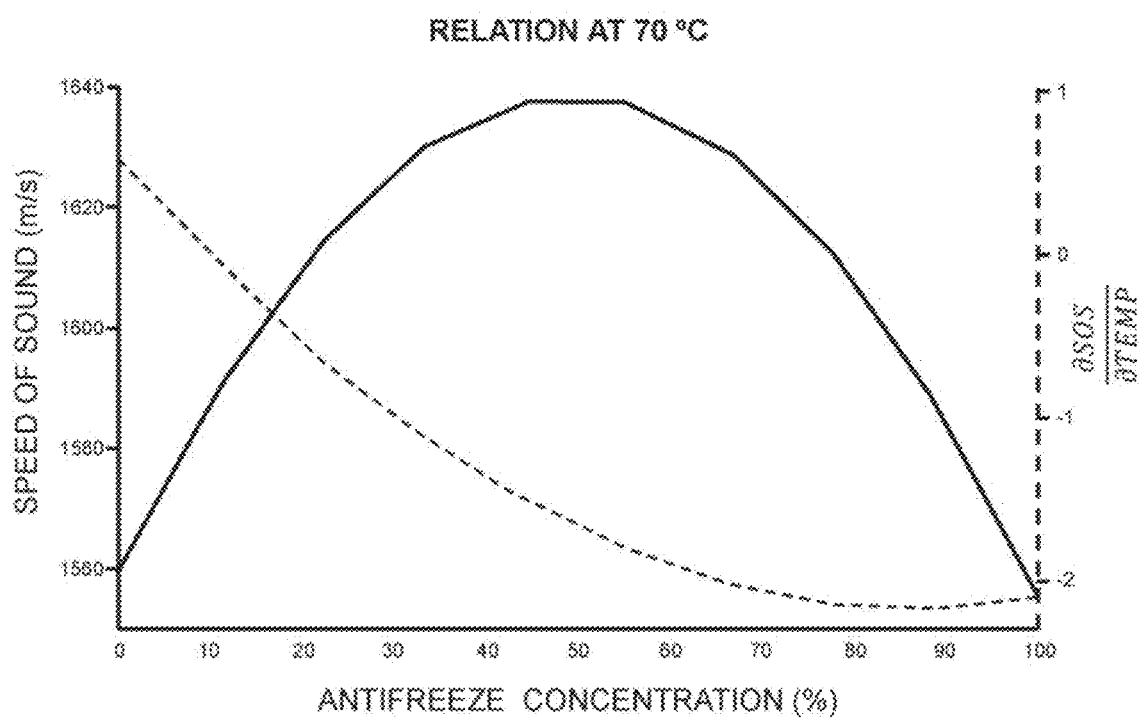
FIG. 4: shows a 2D plot illustrating a relation between antifreeze concentration and speed of sound at a temperature of 70° C., and between antifreeze concentration and a partial derivative of speed of sound with respect to temperature at a temperature of 70° C.

FIG. 4 shows firstly, at 70° C., the relation between antifreeze concentration and speed of sound as an unbroken line in relation to the left vertical axis. This line illustrates a cut through the surface of FIG. 3 at 70° C. It can be seen that the line approximately follows the shape of an inverted parabola. Further, it can be seen that a given speed of sound value is not necessarily sufficient to unambiguously determine a value of the antifreeze concentration in the fluid and likewise, each antifreeze concentration value does not lead to a unique speed of sound value. Secondly, FIG. 4 shows, at 70° C., the relation between antifreeze concentration and the partial derivative of speed of sound with respect to temperature as a dashed line in relation to the right vertical axis. The partial derivative relates to the curvature of the surface of FIG. 3 along a line of constant temperature, where the temperature is 70° C. It can be seen that the curvature is positive for low values of antifreeze concentration and becomes negative for higher values of antifreeze concentration. This partial derivative curve enables an unambiguous solution to be found for antifreeze concentration values approximately between 0% and 60%.

Figure 5:
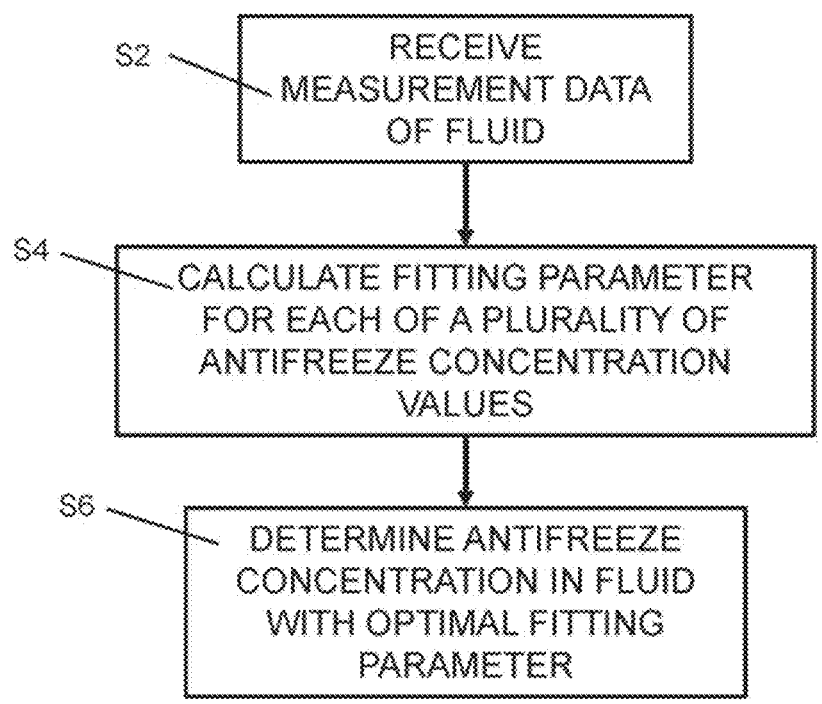
FIG. 5: shows a flow diagram illustrating a sequence of steps for determining antifreeze content in a fluid of an HVAC system.

FIG. 5 shows a flow diagram illustrating a sequence of steps for determining antifreeze content in the fluid of an HVAC system 1.

In a preparatory step S1 (not illustrated), the sensor unit 3 measures the temperature of the fluid and the speed of sound in the fluid and transmits measurement data, comprising the measured temperature of the fluid and the measured speed of sound in the fluid, to the control device 2.

In step S2, the control device 2 receives the measurement data of the fluid from the sensor unit 3. The measurement data of the fluid is stored in the memory 22 and, in an embodiment, is transmitted via the communication interface 23 to the remote server.

In an embodiment, the control device 2 detects whether the measurement data of the fluid has changed. A change in the measurement data is detected by the processor 21, if the measurement data has changed greater than a predetermined amount. For example, if the measured speed of sound changes by more than 20 m/s within a time period of a week, a change is detected by the control device 2 and this change is stored in the memory 22. The detection of the change is, in an embodiment, transmitted by the control device 2 via the communication interface 23 to the remote server. Because the speed of sound depends on the temperature of the fluid, and the temperature of the fluid can vary in the HVAC system 1 over time, the processor 21, using the relation, takes into account variations in the speed of sound due to changes in the temperature when detecting a change. The processor 21 of the control device 2 proceeds beyond step S2 only if a change is detected.

In Step S4, a fitting parameter is calculated for a plurality of antifreeze concentration values. The fitting parameter is calculated using the measurement data. The fitting parameter is also calculated using previous measurement data and/or previous antifreeze concentration data. In particular, the processor 21 of the control device 2 uses the measurement data, along with previous measurement data and/or previous antifreeze concentration data to calculate a fitting parameter for each of the plurality of antifreeze concentration values. The previous measurement data comprises previously measured temperatures of the fluid and previously measured speeds of sound in the fluid, both relating to a plurality of time points extending into the past, for example hourly measurement data extending several days into the past. The previous antifreeze concentration data includes previously determined antifreeze concentration values relating to a plurality of time points extending into the past, as with the previous measurement data. The previous measurement data and/or the previous antifreeze concentration data is either stored in the memory 22 of the control device 2 or retrieved by the control device 2, for example from the local gateway or from the remote server. The plurality of antifreeze concentration values can be generated automatically according to a rule or algorithm, such as in a uniform distribution between antifreeze concentration values of 0% and 100%, or generated randomly.

The fitting parameter indicates how well the antifreeze concentration value agrees with the measurement data, along with the previous measurement data and/or previous antifreeze concentration data. In particular, each fitting parameter indicates how well each corresponding antifreeze concentration value agrees with the measurement data, along with the previous measurement data and/or previous antifreeze concentration data. In an embodiment, the fitting parameter is a residual, which indicates the difference between the antifreeze concentration value and a function of the measurement data, the previous measurement data and/or previous antifreeze concentration data. In an embodiment, the fitting parameter is an error, such as an error variable or error function, which indicates how far the antifreeze concentration value lies from a true antifreeze concentration value of the fluid.

In an embodiment, the fitting parameter is computed by a regression model taking as inputs previous measurement data and/or previous antifreeze concentration data. The predictor is used by the processor 21 to calculate the fitting parameter for each antifreeze concentration value.

In an embodiment, each fitting parameter is calculated using a difference between each antifreeze concentration value and one or more previously determined antifreeze concentration values. Those antifreeze concentration values with a greater difference to one or more past antifreeze concentration values will have a larger associated fitting parameter than those antifreeze concentration values with a smaller difference. In this case a smaller fitting parameter is more optimal.

In an embodiment, the fitting parameter for a particular antifreeze concentration value is calculated by evaluating a sum of differences between the particular antifreeze concentration value and each previously determined antifreeze concentration value.

In an embodiment, the sum is weighted, for example the weighting is in the form of an exponential decay, such that more recent previously determined antifreeze concentration values are weighted more highly than less recent previously determined antifreeze concentration values.

In an embodiment, each fitting parameter is calculated in the processor 21 of the control device 2 using a predictor. The predictor is a variable, function, algorithm, model, or combination thereof, which uses the measurement data, the previous measurement data and/or the previous antifreeze concentration data to determine a predicted antifreeze concentration value. The predictor further uses the measurement data and the relation between temperature, antifreeze concentration, and speed of sound to calculate the fitting parameter for each antifreeze concentration value. The predictor is received by the processor 21 either from the memory 22 or, via the communication interface 23, from the remote server. In an embodiment, the predictor is generated by the processor 21 using previous measurement data and/or previous antifreeze concentration data.

In an embodiment, the predictor is a machine-learning model, for example a neural network. The neural network is trained using training data from a large number of HVAC systems 1, the training data comprising of training measurement data including temperature and speed of sound measurements of a large number of time-points. Additionally, the training data comprises antifreeze content data including the determined antifreeze concentration and/or antifreeze type for the large number of time-points. The processor 21 of the control device 2 uses the neural network to generate a predicted antifreeze concentration value using the previous measurement data and/or the previous antifreeze concentration data. The processor 21 then compares the predicted antifreeze concentration value with each of the plurality of antifreeze concentration values to calculate each fitting parameter.

In an embodiment, the predictor includes a moving average value comprising one or more of: a moving average antifreeze concentration value, a moving average temperature value, or a moving average speed of sound value. More specifically, the moving average value is an average value of the previous measurement data and/or previous antifreeze concentration data in a certain time-window, the time-window extending from the present into the past by a pre-determined number of hours or days, or months, or a certain number of values. In an embodiment, the moving average value is exponentially weighted, such that more recent previous measurement data and/or previous antifreeze concentration data is weighted higher than less recent measurement data and/or previous antifreeze concentration data. The processor 21 is configured to calculate the fitting parameter by comparing the moving average value with the measurement data in view of the relation.

In an embodiment, calculating the fitting parameter for each antifreeze concentration value comprises the processor 21 estimating a predicted speed of sound using the measured temperature and the relation. The relation defines, for each temperature and antifreeze concentration value, a single value for speed of sound. By using the measured temperature and the antifreeze concentration value, the processor 21 estimates a predicted speed of sound. Alternatively, or in addition, the processor 21 uses previous antifreeze concentration data for estimating the predicted speed of sound. This predicted speed of sound is then compared, in the processor 21, to the measured speed of sound and this comparison is used by the processor 21 to calculate the fitting parameter. The larger the deviation between the predicted speed of sound and the measured speed of sound, the larger the fitting parameter.

In an embodiment, calculating the fitting parameter by comparing, in the processor 21, the predicted speed of sound with the measured speed of sound further includes comparing previous speed of sound data with previous predicted speeds of sound. The previous predicted speeds of sound typically vary for each of the plurality of antifreeze concentration values. Namely, to obtain the previous predicted speeds of sound for an (assumed) antifreeze concentration value, previous measurement data such as previously measured temperatures and/or previous measured speed of sounds are used. The optimal fitting parameter therefore also takes into account historical measurement data being obtained in previous iteration loops. A weighted sum of the differences between predicted speeds of sound and measured speeds of sound for a plurality of time points is then used to calculate the fitting parameter. In an embodiment, the weighting is an exponential weighting where more recent time points are weighted greater than less recent time points.

In an embodiment, calculating the fitting parameter for each antifreeze concentration value comprises the processor 21 calculating one or more partial derivatives. For example, partial derivatives of the speed of sound with respect to the temperature are calculated by the processor 21. As illustrated in FIG. 4, the partial derivative of the speed of sound with respect to temperature evaluated at 70° C. has a roughly parabolic shape with a turning point at an antifreeze concentration of approximately 90%. The partial derivative of the speed of sound with respect to the temperature for an index t at a particular antifreeze concentration is calculated, in the processor 21, by computing a difference between successive speeds of sound and dividing this difference by a difference between successive temperatures, as defined by the following formula:

$$\frac{\partial SOS}{\partial TEMP} = \frac{SOS_t - SOS_{t-1}}{TEMP_t - TEMP_{t-1}},$$

where SOS is the speed of sound, TEMP is the temperature, and t is the index of a sequence of speeds of sound and temperatures. A measured partial derivative and a predicted partial derivative are computed, the measured partial derivative computed by the processor 21 using the measured speed of sound, previously measured speeds of sound, the measured temperature, and previously measured temperatures according to the formula above. The predicted partial derivative is computed, in the processor 21, by computing a predicted speed of sound using the measured temperature and the defined relation, and dividing the difference between two successive predicted speeds of sound with a difference between two successive temperature measurements.

In an embodiment, the relation further includes a differentiated relation between the temperature, the concentration and the partial derivative. This is then used to determine the predicted partial derivative.

The measured partial derivative and the predicted partial derivative are computed for each of the antifreeze concentration values, and the processor 21 calculates the fitting parameter for each antifreeze concentration using a difference between the measured partial derivative and the predicted partial derivative.

In an embodiment, calculating the fitting parameter using the difference between the predicted partial derivate and the measured partial derivative further includes the processor 21 comparing previous predicted partial derivatives with previous measured partial derivatives. A weighted sum of differences between predicted partial derivatives and measured partial derivatives of a plurality of time points is used to calculate the fitting parameter. Preferably, the weighting is an exponential weighting where more recent time points are weighted greater than less recent time points.

In an embodiment, the fitting parameter FP for a given antifreeze concentration value CONC is calculated at a particular point in time t using the following function:

$$FP = \alpha \sum_{i=0}^{n} \left| SOS_{t-i} - SOS_{pred,t-i} \right| \quad (1)$$

$$+ \beta \sum_{i=0}^{n} \left| \frac{\partial SOS}{\partial TEMP_{t-i}} - \frac{\partial SOS}{\partial TEMP_{pred,t-i}} \right| + \gamma \sum_{i=1}^{m} |CONC_t - CONC_{t-i}|$$

where $SOS_{t-i}$ is the measured speed of sound, $SOS_{pred,t-i}$ is the predicted speed of sound calculated using the measured temperature and the relation, $$\frac{\partial SOS}{\partial TEMP_{t-i}}$$

is the measured partial derivative as explained above, $$\frac{\partial SOS}{\partial TEMP_{pred,t-i}}$$

is the predicted partial derivative as described above, $CONC_t$ and $CONC_{t-i}$ are previous antifreeze concentration values at times t and t–i, and $\alpha$, $\beta$, $\gamma$ are weights of the first, second, and third terms of the function, respectively. Additionally, each of the three terms can include a weighting function inside the sum which is dependent on the index i. For example, the weighting function is an exponential function such that the weighting decreases for larger i and therefore more recent results are given more weight. The parameters n and m are natural values, which may be distinct from each other. They may be chosen such that the function (1) takes into account previous measurement data and previous antifreeze concentration data of one or more weeks or months, a particular number of samples depending on computational resources, or up until a particular cut-off. This particular cut-off is, in an example, a time-point indicating a refill of the HVAC system 1, as described below. This ensures that the refilling of antifreeze fluid does not lead to skewed future results regarding determining the antifreeze concentration in the fluid.

In step S6, a single antifreeze concentration value is selected with an optimal fitting parameter. The processor 21 of the control device 2 determines the antifreeze concentration value with the optimal associated fitting parameter and this antifreeze concentration value is the determined antifreeze concentration value in the fluid. The antifreeze concentration value is then stored in the memory 22 of the control device 2 by the processor 21. In an embodiment, the antifreeze concentration value is transmitted, by the control device 2, to the remote server.

In an embodiment, the optimal fitting parameter is the smallest fitting parameter.

In an embodiment, after selecting the optimal fitting parameter, a new set of antifreeze concentration values is generated by the processor based on the antifreeze concentration value associated with the optimal fitting parameter. A new set of fitting parameters is then calculated and an optimal fitting parameter of this new set is determined. This optimization process is iterative and enables a fast and efficient generation of antifreeze concentration values. Using the optimization process, the processor then selects the optimal fitting parameter from all the iterations and determines the associated antifreeze concentration value. That antifreeze concentration value is the determined antifreeze concentration value in the fluid.

In an embodiment, the processor 21 receives a refill indicator which indicates a point in time that the fluid in the HVAC system 1 has been refilled. The refill indicator is used by the processor 21 when calculating the fitting parameter. For example, the refill indicator is used by the processor 21 when determining up to which time point in the past previous measurement data and/or previous antifreeze data should be considered when calculating the fitting parameter. This is because an assumption underlying the behavior of the fluid in the HVAC system 1 is that the antifreeze concentration in the fluid varies slowly and continuously over time, and this assumption underlies the fitting parameter calculation in some embodiments. Therefore, receiving the refill indicator enables a more accurate determination of the antifreeze concentration in the fluid as the processor 21 has information relating to (relatively) fast and abrupt changes in the antifreeze concentration in the fluid. In an embodiment, previous measurement data and/or previous antifreeze concentration data corresponding to points of time further in the past than the point in time indicated by the refill indicator is not considered when calculating the fitting parameter. The refill indicator, in an embodiment, further includes an indicator of a volume of fluid refilled and/or a type of fluid which was refilled, and the processor 21 uses the volume of fluid refilled and/or the type of fluid refilled to calculate the fitting parameter.

In an embodiment, the processor 21 determines a change in the antifreeze concentration value of the fluid by comparing the determined antifreeze concentration value of step S4 with previous antifreeze concentration values. If the difference between the determined antifreeze concentration value is greater than a predetermined threshold within a predetermined time period, then the processor 21 determines the change. Responsive to determining the change, the processor 21 generates a message indicating the change in antifreeze concentration value in the fluid. The message comprises one or more of: the determined antifreeze concentration value, a timestamp indicating a time the measurement data was received, or a difference relative to a previous antifreeze concentration value. Likewise, if the antifreeze type was also determined to be different from a previous antifreeze type, the message further indicates the change in antifreeze type. The message is stored in the memory 22 and/or transmitted via the communication interface 23 to the remote server, enabling a technician to verify whether the HVAC system 1 is still operating according to specification or whether maintenance or service is required. Further, a long term trend of the antifreeze concentration value in the fluid can be calculated. This long term trend can be used for predictive maintenance and/or for generating early warning messages. For example, the long term trend can indicate that the antifreeze concentration value is consistently decreasing and that maintenance must be performed within a certain time period, or that the antifreeze concentration value in the fluid is not sufficient for the HVAC system 1 to operate reliably through winter.

Figure 6:
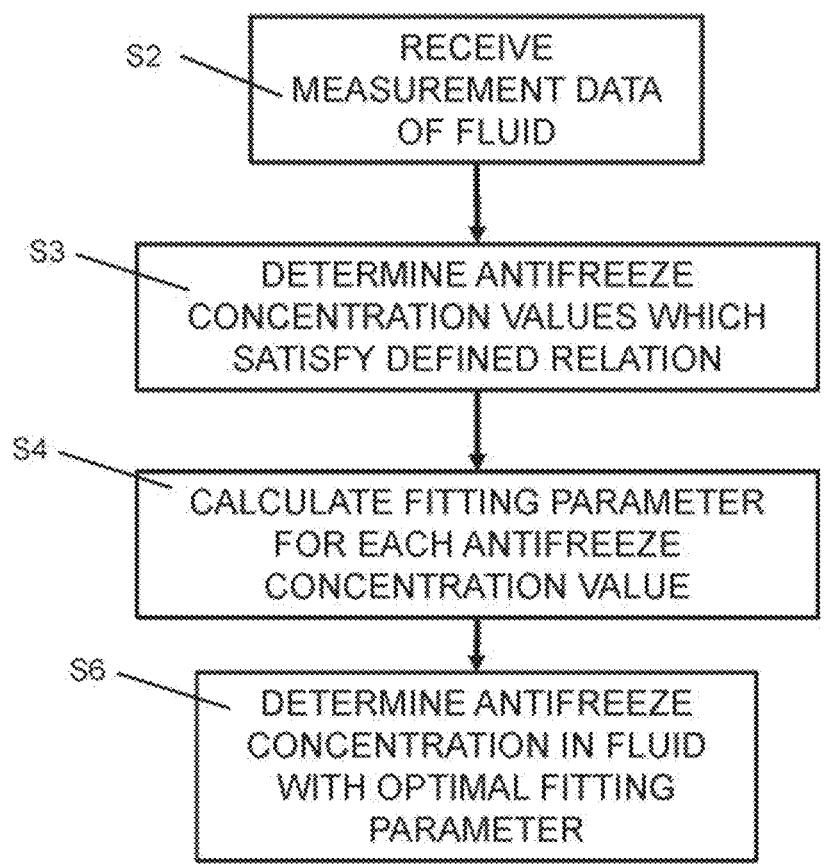
FIG. 6: shows a flow diagram illustrating a sequence of steps for determining antifreeze content in a fluid of an HVAC system.

FIG. 6 shows a flow diagram illustrating a sequence of steps for determining antifreeze content in the fluid of an HVAC system 1.

In step S3, the control device 2 determines one or more antifreeze concentration values which satisfy the defined relation (see FIG. 3) and the measurement data. In particular, the control device 2 determines one or more points in the set of points which match the measured data, i.e. points which have the same or approximately the same temperature and speed of sound as the measured temperature and the measured speed of sound. From the one or more points, one or more corresponding antifreeze concentration values are determined. For example, if the measured temperature is 70° C., the measured speed of sound is 1620 m/s, and the moving average value of the antifreeze concentration value is 25%, then according to the relation (see FIG. 4), one of the antifreeze concentration values is approximately 28%, another antifreeze concentration value being approximately 72%. The processor 21 then associates a smaller fitting parameter with the antifreeze concentration value 28% than with the antifreeze concentration value 72%.

In an embodiment, the processor 21 generates interpolated points which lie between known points of the relation. These interpolated points are then matched to the measured data.

In an embodiment, a tolerance range may be used by the control device 2 to determine the one or more matching points and therefore the one or more antifreeze concentration values. The tolerance range accounts for a measurement uncertainty in the measured temperature and the measured speed of sound. The tolerance range comprises a temperature tolerance value and a speed of sound tolerance value. The tolerance range is generated by a function dependent on both the measured temperature and the measured speed of sound. This tolerance range may be illustrated as a tolerance ellipse whose major and minor axes correspond to the temperature tolerance value and the speed of sound tolerance value, respectively. Additionally, due to the changing curvature of the relation, at particular temperatures and speeds of sound, either the measured temperature or the measured speed of sound may allow for a more accurate determination of antifreeze concentration values than the other.

Depending on the measured temperature and the measured speed of sound, one or more antifreeze concentration values are determined which satisfy the relation and the measurement data. In an embodiment, the tolerance range around the measurement data is used to determine which antifreeze concentration values satisfy the relation. In an embodiment, all antifreeze concentration values which satisfy the relation and the measurement data are determined. The antifreeze concentration values are adjacent to each other or nonadjacent. The antifreeze concentration values are considered adjacent if all antifreeze concentration values are grouped together in a single cluster, for example within the range 40-60%. This is for example the case when the measured temperature is approximately 70° C. and the measured speed of sound is approximately 1640 m/s (see FIG. 4). This large range of antifreeze values is due to an inflection point in the function of the speed of sound with respect to antifreeze concentration at 70° C. Antifreeze concentration values are considered nonadjacent if the antifreeze concentration values are not grouped together in a single cluster but arranged in a plurality of clusters, for example within two ranges of 15-20% and 80-85%. This is the case when, for example, the measured temperature is approximately 70° C. and the measured speed of sound is approximately 1600 m/s. This case arises due to the parabolic shape of the function of the speed of sound with respect to antifreeze concentration at 70° C. as there is more than one antifreeze value (or more than one group of antifreeze values within the tolerance range) which satisfies the relation.

Figure 7:
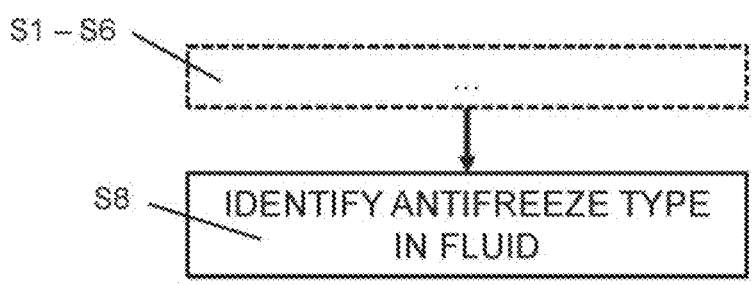
FIG. 7: shows a flow diagram illustrating a sequence of steps for determining antifreeze content in a fluid of an HVAC system.
Figure 8:
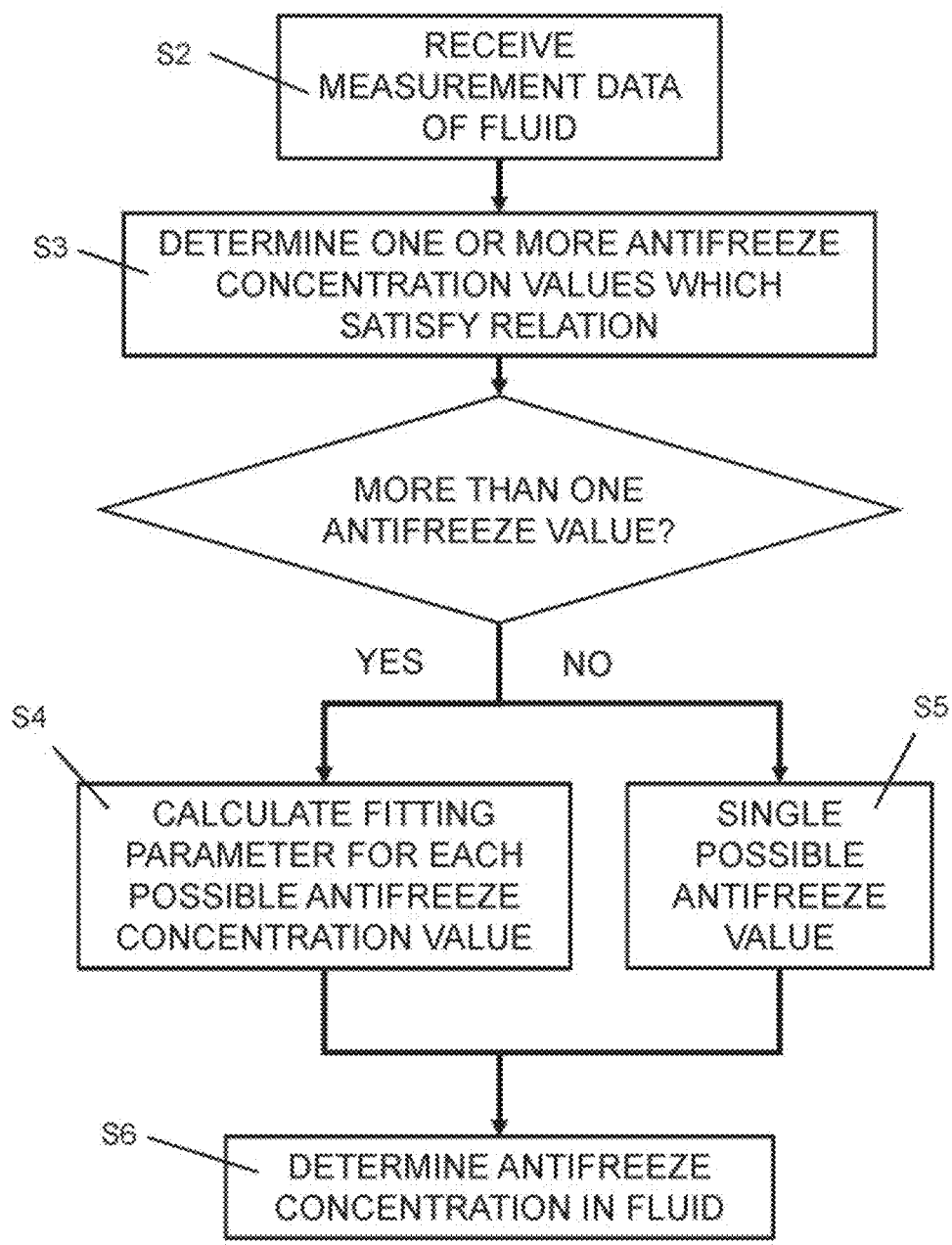
FIG. 8: shows a flow diagram illustrating a sequence of steps for determining antifreeze content in a fluid of an HVAC system.

In FIG. 7, one or more of steps S1-S6, which relate to steps S1, S2, S3, S4, and S6 as described above for FIGS. 5 and 6, and optional step S5 as described below for FIG. 8, are carried out for a plurality of relations, each relation being assigned to a particular antifreeze type. In step S8, the control device 2 identifies the antifreeze type in the fluid using the relation which is associated with the smallest, respectively the optimal, fitting parameter. For example, the antifreeze concentrations for the antifreeze type propylene glycol may have larger associated fitting parameters than the fitting parameter associated with antifreeze concentrations for the antifreeze type ethylene glycol, and therefore in this example, the processor 21 of the control device 2 would determine the antifreeze type to be ethylene glycol. The control device 2 stores the identified antifreeze type in the memory 22 and, in an embodiment, transmits a message indicated the identified antifreeze type to the remote server.

FIG. 8 shows an embodiment where the processor 21 checks whether one antifreeze concentration value was determined in step S2, or whether more than one antifreeze concentration value was determined. If only one antifreeze concentration value was determined, then in step S5 that single antifreeze concentration value is taken by the processor 21 to be the determined antifreeze concentration value in the fluid. If more than one antifreeze concentration value was determined, then in step S4 the fitting parameter is calculated for each antifreeze concentration value as described above in relation to FIG. 5, and also for step S6 the antifreeze concentration value is determined by the processor as also described above in relation to FIGS. 5 and 6.

Figure 9:
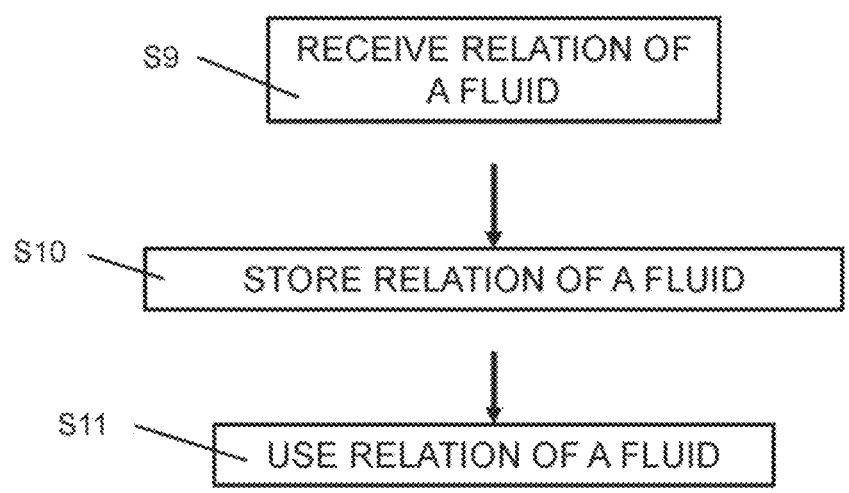
FIG. 9: shows a flow diagram illustrating a sequence of steps for receiving a relation of a fluid.

In FIG. 9, step S9, a relation of a fluid is received. The relation of the fluid is received by a device of the HVAC system 1, in particular by the control device 2 using the communication interface 23. The relation of the fluid may be received by the control device 2 after installation and/or commissioning of the HVAC system 1. The relation is received from the local gateway, from the remote server, or from another data storage system.

In an embodiment, in a preparatory step (not shown), the HVAC system 1 transmits a request for a relation of a fluid to the local gateway, to the remote server, or to another data storage system. The request comprises measurement data of the fluid and optionally a determined antifreeze concentration in the fluid. Depending on the embodiment, the request is transmitted if the HVAC system 1 cannot identify the antifreeze type in the fluid, or if the HVAC system 1 determines that none of the stored relations, each associated with a particular antifreeze type, match the measurement data and/or the determined antifreeze concentration.

The relation is stored in the memory 22 of the control device 2 in step S10. Thereby, new fluids having a new type of antifreeze, which did not have a relation previously stored in the memory 22, can be added and used in the HVAC system 1. In particular, the relation can be received and stored, which relation was not stored on the device during installation, commissioning, or otherwise setting up or initially configuring the HVAC system 1. This has the advantage that relations of newly developed antifreeze fluids, in particular antifreeze fluids which did not yet exist during installation and commissioning of the HVAC system 1, or which had not yet been measured and characterized (i.e. for which a relation had not yet been established), can be added and used in the HVAC system 1. These newly developed antifreeze fluids include antifreeze fluids developed specifically according to requirements of the HVAC system 1.

In step S11, the control device 2 implements and uses the relation. In particular, the control device 2 is configured to determine an antifreeze concentration in the fluid using the relation according to a method described herein.

It should be noted that, in the description, the sequence of the steps has been presented in a specific order, one skilled in the art will understand, however, that the order of at least some of the steps could be altered, without deviating from the scope of the invention.

The invention claimed is:

1. A method for determining antifreeze content in a fluid of a heating, ventilation, and air conditioning (HVAC) system, performed by the HVAC system, the HVAC system comprising a control device and a sensor unit operatively connected to the control device, the method comprising:
    measuring, by the sensor unit, the measurement data of the fluid;
    receiving, in a processor of the control device, using a communication interface of the control unit, measurement data of the fluid measured by the sensor unit, the measurement data comprising a measured temperature of the fluid and a measured speed of sound in the fluid;
    retrieving, in the processor, from a non-volatile memory of the control device, a defined relation between antifreeze concentration, temperature, and speed of sound;
    calculating, in the processor, for each of a plurality of antifreeze concentration values a fitting parameter, as a function of:
    the measurement data and the defined relation, and at least one of: previous measurement data of the fluid of the HVAC system or previous antifreeze concentration data of the fluid of the HVAC system,
    each fitting parameter indicative of how well the antifreeze concentration value agrees with the measurement data and at least one of: the previous measurement data or the previous antifreeze concentration data; and
    determining, in the processor, an antifreeze concentration in the fluid by selecting the antifreeze concentration value with an optimal fitting parameter, the optimal fitting parameter being a particular fitting parameter related to a best fit between the antifreeze concentration value, the measurement data and at least one of: the previous measurement data or the previous antifreeze concentration data.

2. The method of claim 1, wherein the calculating comprises:
    calculating, in the processor, for an initial set of antifreeze concentration values an initial set of fitting parameters;
    generating, in the processor, using the antifreeze concentration value of the initial set of antifreeze concentration values with an optimal fitting parameter, a subsequent set of antifreeze concentration values;
    calculating, in the processor, using the subsequent set of antifreeze concentration values a subsequent set of fitting parameters; and
    determining, in the processor, the antifreeze concentration in the fluid by selecting the antifreeze concentration value of the subsequent set of antifreeze concentration values with a subsequent optimal fitting parameter.

3. The method of claim 1, further comprising determining, in the processor, using the measurement data, the plurality of antifreeze concentration values such that each of the plurality of antifreeze concentration values satisfies the defined relation among the antifreeze concentration, the temperature, and the speed of sound.

4. The method of claim 1, wherein each antifreeze concentration value is associated with an antifreeze type, and the method further comprises identifying the antifreeze type in the fluid by determining, in the processor, the antifreeze type associated with the determined antifreeze concentration.

5. The method of claim 1, wherein the calculating comprises:
    calculating, in the processor, a predictor using the previous measurement data and/or previous antifreeze concentration data, and
    comparing, in the processor, the predictor with the measurement data and/or the antifreeze concentration values.

6. The method of claim 1, wherein the calculating comprises:
    estimating, in the processor, a predicted speed of sound using the measured temperature and the defined relation, and
    comparing, in the processor, the predicted speed of sound with the measured speed of sound.

7. The method of claim 1, wherein the method further comprises:
    determining, in the processor, a change in the antifreeze concentration in the fluid by comparing the selected antifreeze concentration value with one or more previous antifreeze concentration values; and
    generating, in the processor, a message indicating the change in antifreeze concentration value in the fluid.

8. A device for determining antifreeze content in a fluid of a heating, ventilation, and air conditioning (HVAC) system, the deice comprising a processor configured to:
    receive measurement data of the fluid measured by a sensor unit, the measurement data comprising a measured temperature of the fluid and a measured speed of sound in the fluid;
    retrieve a defined relation between antifreeze concentration, temperature, and speed of sound;
    calculate, for each of a plurality of antifreeze concentration values a fitting parameter, as a function of:
    the measurement data and the defined relation, and at least one of: previous measurement data of the fluid of the HVAC system or previous antifreeze concentration data of the fluid of the HVAC system,
    each fitting parameter indicative of how well the antifreeze concentration value agrees with the measurement data and at least one of: the previous measurement data or the previous antifreeze concentration data; and
    determine the antifreeze concentration in the fluid by selecting the antifreeze concentration value with an optimal fitting parameter, the optimal fitting parameter being a particular fitting parameter related to a best fit between the antifreeze concentration value, the measurement data and at least one of: the previous measurement data or the previous antifreeze concentration data.

9. The device of claim 8, wherein the processor is configured to calculate the fitting parameter by:
    calculating, for an initial set of antifreeze concentration values an initial set of fitting parameters;
    generating, using the antifreeze concentration value of the initial set of antifreeze concentration values with an optimal fitting parameter, a subsequent set of antifreeze concentration values;
    calculating, using the subsequent set of antifreeze concentration values a subsequent set of fitting parameters; and
    determining, the antifreeze concentration in the fluid by selecting the antifreeze concentration value of the subsequent set of antifreeze concentration values with a subsequent optimal fitting parameter.

10. The device of claim 9, wherein to calculate the fitting parameter for each antifreeze concentration value the processor is configured to:
   estimate a predicted speed of sound using the measured temperature and the defined relation, and
   compare the predicted speed of sound with the measured speed of sound.

11. The device of claim 8, wherein the processor is further configured to determine, using the measurement data, the plurality of antifreeze concentration values such that each of the plurality of antifreeze concentration values satisfies the defined relation among the antifreeze concentration, the temperature, and the speed of sound.

12. The device of claim 8, wherein each antifreeze concentration value is associated with an antifreeze type; and the processor is further configured to identify the antifreeze type in the fluid by determining the antifreeze type associated with the determined antifreeze concentration.

13. The device of claim 8, wherein to calculate the fitting parameter the processor is configured to:
   calculate a predictor using the previous measurement data and/or previous antifreeze concentration data, and
   compare the predictor with the measurement data and/or the antifreeze concentration values.

14. A computer readable storage medium having stored thereon computer program code which, when executed by a processor of a device, causes the device to at least:
   receive measurement data of the fluid measured by a sensor unit, the measurement data comprising a measured temperature of the fluid and a measured speed of sound in the fluid;
   retrieve a defined relation between antifreeze concentration, temperature, and speed of sound;
   calculate, for each of a plurality of antifreeze concentration values a fitting parameter as a function of: the measurement data and at least one of: previous measurement data and a defined relation between antifreeze concentration, temperature, and speed of sound or previous antifreeze concentration data of the fluid of the HVAC system,
   each fitting parameter indicative of how well the antifreeze concentration value agrees with the measurement data and at least one of: the previous measurement data or the previous antifreeze concentration data; and
   determine the antifreeze concentration in the fluid by selecting the antifreeze concentration value with an optimal fitting parameter, the optimal fitting parameter being a particular fitting parameter related to a best fit between the antifreeze concentration value, the measurement data and at least one of: the previous measurement data or the previous antifreeze concentration data.

15. A method for determining antifreeze content in a fluid of a heating, ventilation, and air conditioning (HVAC) system, the method comprising:
   receiving, in a processor, measurement data of the fluid measured by a sensor unit, the measurement data comprising a measured temperature of the fluid and a measured speed of sound in the fluid;
   calculating, in the processor, for each of a plurality of antifreeze concentration values a fitting parameter as a function of:
   the measurement data and the defined relation, and
   at least one of: previous measurement data of the fluid of the HVAC system or previous antifreeze concentration data of the fluid of the HVAC system,
   each fitting parameter indicative of how well the antifreeze concentration value agrees with the measurement data and at least one of: the previous measurement data or the previous antifreeze concentration data; and
   determining, in the processor, an antifreeze concentration in the fluid by selecting the antifreeze concentration value with an optimal fitting parameter, the optimal fitting parameter being a particular fitting parameter related to a best fit between the antifreeze concentration value, the measurement data and at least one of: the previous measurement data or the previous antifreeze concentration data; and
   generating, in the processor, a control signal depending on the antifreeze concentration in the fluid, the control signal configured to control an actuator of the HVAC system to alter the opening or closing of a valve controlled by the actuator.

* * * * *